(12) United States Patent
Shaver

(10) Patent No.: US 11,685,706 B2
(45) Date of Patent: Jun. 27, 2023

(54) PROCESS FOR CONTINUOUS ACETIC ACID PRODUCTION

(71) Applicant: CELANESE INTERNATIONAL CORPORATION INC., Irving, TX (US)

(72) Inventor: Ronald D. Shaver, Houston, TX (US)

(73) Assignee: CELANESE INTERNATIONAL CORPORATION, Irving, TX (US)

(*) Notice: Subject to any disclaimer, the term of this patent is extended or adjusted under 35 U.S.C. 154(b) by 298 days.

(21) Appl. No.: 17/021,576

(22) Filed: Sep. 15, 2020

(65) Prior Publication Data

US 2020/0407305 A1 Dec. 31, 2020

Related U.S. Application Data

(62) Division of application No. 16/178,903, filed on Nov. 2, 2018, now Pat. No. 10,807,935.

(51) Int. Cl.
| | |
|---|---|
| *C07C 51/12* | (2006.01) |
| *C07C 51/44* | (2006.01) |
| *C07C 53/08* | (2006.01) |
| *B01J 19/00* | (2006.01) |

(52) U.S. Cl.
CPC .......... *C07C 51/12* (2013.01); *B01J 19/0006* (2013.01); *C07C 51/44* (2013.01); *B01J 2219/00162* (2013.01); *B01J 2219/00164* (2013.01); *C07C 53/08* (2013.01)

(58) Field of Classification Search
USPC ...................................................... 562/519
See application file for complete search history.

(56) References Cited

U.S. PATENT DOCUMENTS

| | | | |
|---|---|---|---|
| 5,352,415 A | 10/1994 | Ochiai et al. | |
| 5,625,095 A | 4/1997 | Miura et al. | |
| 6,552,221 B1 | 4/2003 | Hallinan et al. | |
| 6,599,348 B2 | 7/2003 | Chosnek et al. | |
| 6,642,413 B2 | 11/2003 | Thiebaut | |
| 7,052,657 B2 | 5/2006 | Nakajima et al. | |
| 7,223,883 B2 | 5/2007 | Picard et al. | |
| 9,006,483 B2 | 4/2015 | Shimizu et al. | |
| 9,512,056 B2 | 12/2016 | Scates et al. | |
| 9,776,941 B2 | 10/2017 | Shimizu et al. | |
| 2006/0093535 A1 | 5/2006 | Nakajima et al. | |
| 2009/0270651 A1 | 10/2009 | Zinobile | |
| 2011/0021816 A1 | 1/2011 | Scates et al. | |
| 2015/0368176 A1 | 12/2015 | Miura et al. | |
| 2017/0349521 A1 | 12/2017 | Shimizu et al. | |
| 2018/0201564 A1 | 7/2018 | Shimizu et al. | |
| 2018/0230077 A1 | 8/2018 | Miura et al. | |

FOREIGN PATENT DOCUMENTS

| | | |
|---|---|---|
| CN | 1651388 A | 8/2005 |
| CN | 104450988 A | 3/2015 |
| WO | 200204394 A | 1/2002 |

OTHER PUBLICATIONS

International Search Report for PCT/US2019/059336, dated Feb. 5, 2020.
"Process of 200 ktpa Methanol Low Press Oxo Synthesis AA", Swrdici, 2006, pp. 1-37.
International Preliminary Report on Patentability for PCT/US2019/059336 dated Apr. 27, 2021, all pages.

*Primary Examiner* — Ana Z Muresan

(74) *Attorney, Agent, or Firm* — Kilpatrick Townsend & Stockton LLP

(57) ABSTRACT

A process for producing acetic acid that involves operating the flash vessel and first column at the lowest possible pressure for a given production rate is described. Low pressures are achieved by operating on a back pressure established by a vapor discharge from an absorbing system. This reduces the pressure differential to allow steady and efficient acetic acid production.

14 Claims, 2 Drawing Sheets

PROCESS FOR CONTINUOUS ACETIC ACID PRODUCTION

This application is a divisional application of U.S. application Ser. No. 16/178,903, filed on Nov. 2, 2018, the entirety of which is incorporated herein by reference.

FIELD OF THE INVENTION

This invention relates generally to a process for continuous acetic acid production, in particular, to improved processes for producing acetic acid steadily and safely using an effective pressure in the flash vessel and the light ends column.

BACKGROUND OF THE INVENTION

The methanol carbonylation process is known as a suitable industrial synthesis process for acetic acid. The carbonylation process is carried out under low pressures of less than 40 atm in the presence of a Group VIII metal catalyst, such as rhodium, iridium and/or cobalt. A production plant for the methanol carbonylation process typically includes units, such as reactors, flash vessels, distillation columns, absorbers, and guard beds. Acetic acid is typically produced through the plant as follows. In the reactor, acetic acid is continuously formed by introducing methanol and carbon monoxide into a reaction medium containing the metal catalysts, water, methyl iodide, and co-catalysts. Gases are vented from the reactor to control the pressure of the reactor. A portion of the reaction medium is continuously withdrawn and introduced, with or without heat, into a flash vessel that is maintained at a pressure considerably lower than the reactor. The reduction in pressure flashes a vapor product stream comprising the acetic acid that is to be recovered as the product after further purification. The vapor product stream passes through a series of distillation columns to remove impurities and return components of the reaction medium to the reactor. Vents from the process are treated in absorbers to recover components of the reaction medium before discharging. Guard beds can further be used to remove impurities. This process has been found to be effective in producing high purity acetic acid with few impurities.

Various process controls have been described in the literature.

U.S. Pat. No. 7,052,657 describes a process that supplies methanol and carbon monoxide to a liquid phase reaction system including a carbonylation catalytic system, and maintaining a substantially constant liquid level of the reaction system, part of the reaction mixture containing the produced acetic acid is drawn out from the reaction system and supplied to a flash distillation column, and the high boiling point component, which contains the carbonylation catalytic system that has been separated by the flash distillation, is circulated to the reaction system by means of a circulation line. At circulation line, the flow rate is detected by a flow rate sensor and the temperature is detected by a temperature sensor, and based on the detection data, a control unit is used to control the temperature of the circulated high boiling point component by means of a temperature regulating unit and thereby to suppress temperature and pressure fluctuations of the above-mentioned reaction system. US Pub. No. 2006/0093535 also describes a similar process for restraining and stabilizing the temperature and pressure fluctuations in a liquid phase reaction system.

U.S. Pat. No. 5,352,415 describes a process to control the liquid levels in a reactor-flasher combination used particularly for the carbonylation of methanol to acetic acid. Liquid level control is achieved by proportional controllers or other controllers which do not continuously seek zero off-set from the desired level and which proportionally change the liquid flow rates from the respective reactor and flasher. An adjustment can be made to the level controllers to change the liquid flow rates by a function generator which adjusts the flow rate, according to an empirically derived function which correlates changes in methanol feed rate to liquid flow rates from the reactor and flasher.

U.S. Pat. No. 6,642,413 describes a continuous preparative process, including monitoring production, for acetic acid, methyl acetate or a mixture thereof, by carbonylation, in an industrial installation, of methanol or a carbonylatable derivative of methanol with carbon monoxide in a liquid phase in the presence of water and a homogeneous catalyst system. In the process, the reactor temperature and feed rate of the methanol or carbonylatable derivative in said reactor are brought under control of the carbon monoxide feed rate and of at least one of the parameters defining the composition of the reaction medium, or of the venting or of both the reaction medium and of the venting.

U.S. Pat. No. 6,552,221 describes a method of real time process control in a reaction system for the production of acetic acid from the carbonylation of methanol. Reaction system samples are collected from columns and/or transfer lines downstream of a reactor vessel, and the concentration of one or more components in the sample is measured by an infrared analyzer. The concentration measurements are then used to make adjustments in the concentration of components in the reaction system, directly or indirectly, such as by adjusting the temperature profile in a particular column, the flow rate of solution in to or out of a column, the vent gas rate out of the reactor or a column, or the addition or extraction of a component to or from the solution. For optimum process control, the measurements are transmitted to a control unit for real time analysis, and the adjustments are made substantially instantly after the infrared analysis.

Although existing carbonylation processes are highly efficient, further improvements for the recovery of acetic acid in a safe and efficient manner continue to be desirable.

SUMMARY OF THE INVENTION

This invention generally relates to processes for the production of acetic acid by operating the flash vessel and light ends column with a low differential pressure. In some embodiments, there is provided a process for producing acetic acid comprising carbonylating methanol or a methanol derivative in a reactor in the presence of a metal catalyst, iodide salt, water, and methyl iodide to form a reaction medium comprising acetic acid and separating the reaction medium in a flash vessel into a liquid recycle stream and a vapor product stream comprising acetic acid. A portion of the vapor product stream is distilled in a light ends column into an overhead and a side stream comprising acetic acid. The overhead is then partially condensed, at a temperature from 20° C. to 45° C., to form a liquid stream and gaseous stream. A portion of the gaseous stream is withdrawn to an absorption system, and the process comprises regulating a vapor discharge from the absorption system to control the pressure in the flash vessel and the light ends column. Thus, the internal pressure in the flash vessel, operating without a discrete pressure control valve, may be in a range from 0.5 to 5 atm (gauge) and the pressure in a top portion of the light ends column, also without a discrete pressure control valve, may be range from 0.5 to 4 atm. The absorption system may comprise a low pressure absorption tower or high pressure absorption tower and a low pressure absorption tower. The vapor discharge may be controlled from the low pressure absorption tower. In some embodiments, the pressure in a top portion of the low pressure absorption tower is in a range from 0 to 3 atm (gauge).

In addition to the gaseous portion from the partially condensed of the overhead, other vent streams from the reactor and/or flash vessel may be directed to the absorption towers. These vent streams are typically the non-condensable gaseous portions. In the absorption system, one or more absorbent liquids to the absorption system may be used in each tower. One or more valves are used to regulate the vapor discharge from the absorption system and may be controlled by setting a reference value for operating the one or more valves to control a flow rate of the vapor discharge.

In some embodiments, there is provided process for producing acetic acid comprising introducing methanol to a reactor at a first mass flow rate and carbonylating the methanol in the reactor in the presence of a metal catalyst, iodide salt, water, and methyl iodide to form a reaction medium comprising acetic acid. The reaction medium is withdrawn at a second mass flow rate and is separated in a flash vessel into a liquid recycle stream and a vapor product stream comprising acetic acid and the process comprises adjusting the internal pressure of the flash vessel to maintain a mass flow ratio of the second mass flow rate to the first mass flow rate of less than or equal to 10, e.g., from 1 to 10.

BRIEF DESCRIPTION OF THE DRAWINGS

The present invention will be better understood in view of the appended non-limiting figures, wherein.

DETAILED DESCRIPTION OF THE INVENTION

Figure 1:
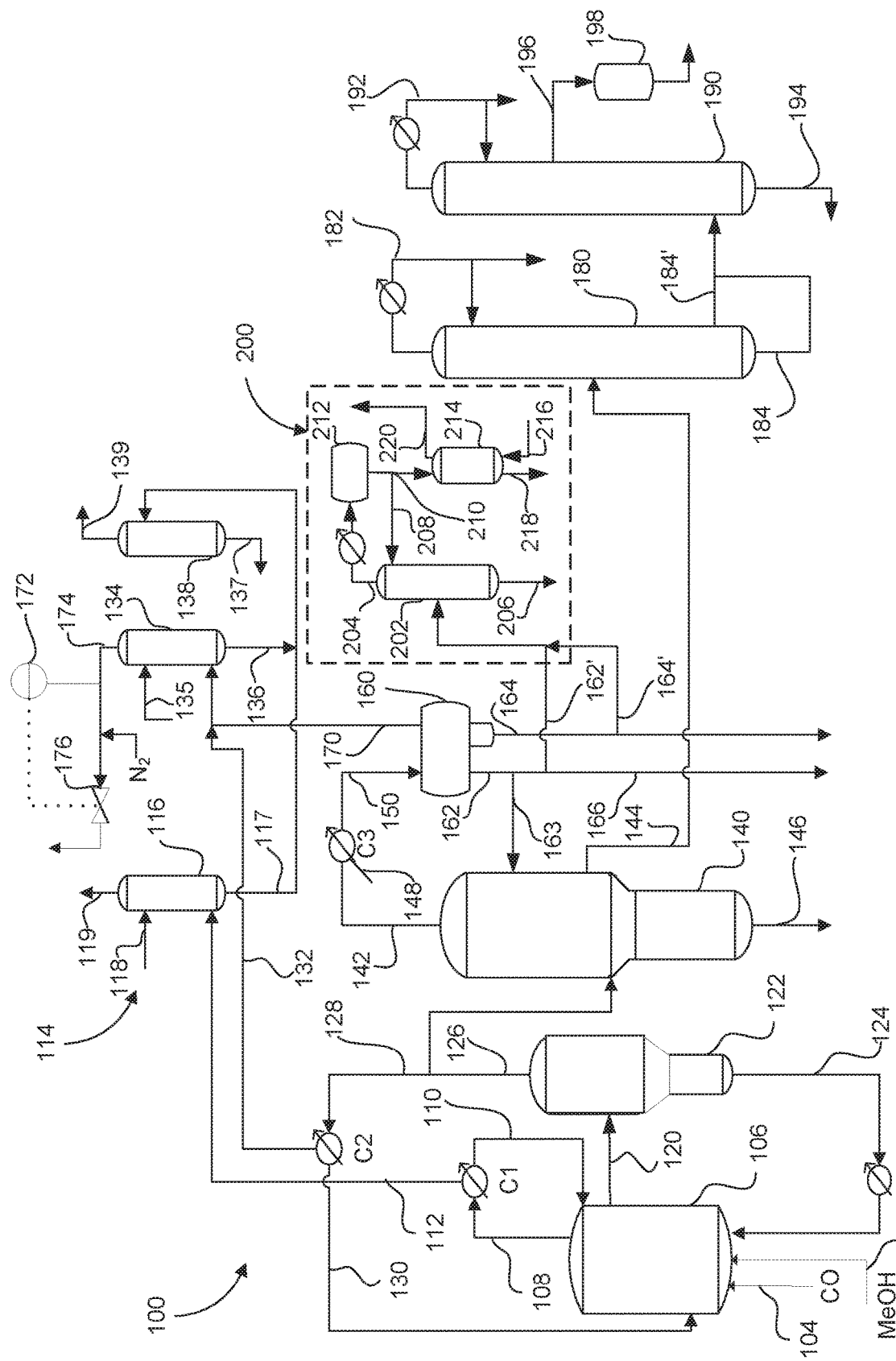
FIG. 1 illustrates a process for producing acetic acid having a valve on the vapor discharge to control the pressure of the flash vessel and first column, in accordance with embodiments of the present invention.

In general, the present invention relates to continuous acetic acid production. In order to achieve steady operation of the carbonylation process for continuous acetic acid production, the pressure in the flash vessel and the first column, e.g., the light ends column, must be regulated. Pressure regulation is for both safety reasons and for efficiency. To achieve efficiency while maintaining safety, the continuous process should be operated at relatively low pressure in the flash vessel and the first column. The carbonylation reactor operates at a greater pressure than the flash vessel, and to separate the acetic acid, the pressure is dropped in the flash vessel. The first column, which is typically the light ends column, receives a vapor product stream from the flash vessel and operates at a lower pressure than the flash vessel. Operating both the flash vessel and light ends column at low pressure reduces the pressure drop between the equipment. This, in turn, results in more efficient flash vessel conditions by providing a vapor product stream to the light ends column with maximized acetic acid content while also resulting in the minimum recirculation of liquid catalyst from the flash vessel back to the reactor.

In contrast, having a large pressure drop between the flash vessel and light ends column can result in decreasing the content of acetic acid in the vapor product stream. This causes the equipment to operate at higher pressures for a given operating rate. Larger pressure drops are also associated with dedicated pressure control units for flash vessel and light ends column, which is to be avoided by the embodiments of the present invention. This is because each vessel needs to operate at a slightly higher pressure for the dedicated pressure control to function.

As described herein by the various embodiments, to operate efficiently, the pressure in the flash vessel and light ends column needs to be adjusted as the production rates change. For example, as production rates increase, the pressure of the flash vessel and light ends column needs to correspondingly increase. Similarly, during production cutbacks, lower pressures may be used to avoid the loss of raw materials and decrease liquid catalyst recycle. Operating at a set pressure, regardless of production rates, results in inefficiencies throughout the process and thus is undesirable.

Thus, in some embodiments, there is provided a process for producing acetic acid comprising introducing methanol to a reactor at a first mass flow rate, carbonylating the methanol in the reactor in the presence of a metal catalyst, iodide salt, water, and methyl iodide to form a reaction medium comprising acetic acid, separating the reaction medium in a flash vessel into a liquid recycle stream and a vapor product stream comprising acetic acid at a second mass flow rate, and adjusting the internal pressure of the flash vessel to maintain a mass flow ratio of the second mass flow rate to the first mass flow rate of less than or equal to 10, e.g., from 1 to 10, from 4 to 10 or from 5 to 9.5. The internal pressure (gauge) in the flash vessel may be adjusted within a range from 0.5 to 5 atm, e.g. 0.5 to 2 atm, or from 0.5 to 1.5 atm. Acetic acid may be obtained by further processing the vapor product stream as described herein.

In some embodiments, a pressure control unit is arranged at the top of an absorbing tower for detecting the pressure of the vapor discharge, e.g., overhead stream. The absorbing tower receives a vent or vapor stream from the flash vessel or first column, or from both. Other vent streams from within the process may also be processed in the absorbing tower. In some embodiments, when the detected pressure exceeds a reference value, the pressure control unit sends a control signal to open the control valve, thereby regulating the vapor discharge pressure. In regulating the vapor discharge, the pressure of the flash vessel and light ends column operates on the established back pressure from the vapor discharge of the tower. When operating on the establishing back pressure, the process can eliminate individual pressure control units for the flash vessel and first column. This reduces the equipment required to safely produce acetic acid. In addition, when operating on the back pressure, the pressure in the flash vessel and light ends column may operate at a lower pressure for a given operating rate.

Thus, in some embodiments, there is provided a process for producing acetic acid comprising carbonylating methanol or a methanol derivative in a reactor in the presence of a metal catalyst, iodide salt, water, and methyl iodide to form a reaction medium comprising acetic acid, separating the reaction medium in a flash vessel into a liquid recycle stream and a vapor product stream comprising acetic acid, distilling a portion of the vapor product stream in a light ends column into an overhead and a side stream comprising acetic acid, partially condensing the overhead into a liquid stream and gaseous stream, withdrawing a portion of the gaseous stream to an absorption system, and regulating a vapor discharge from the absorption system to control the pressure in the flash vessel and the first column.

Carbonylation Reaction

Figure 2:
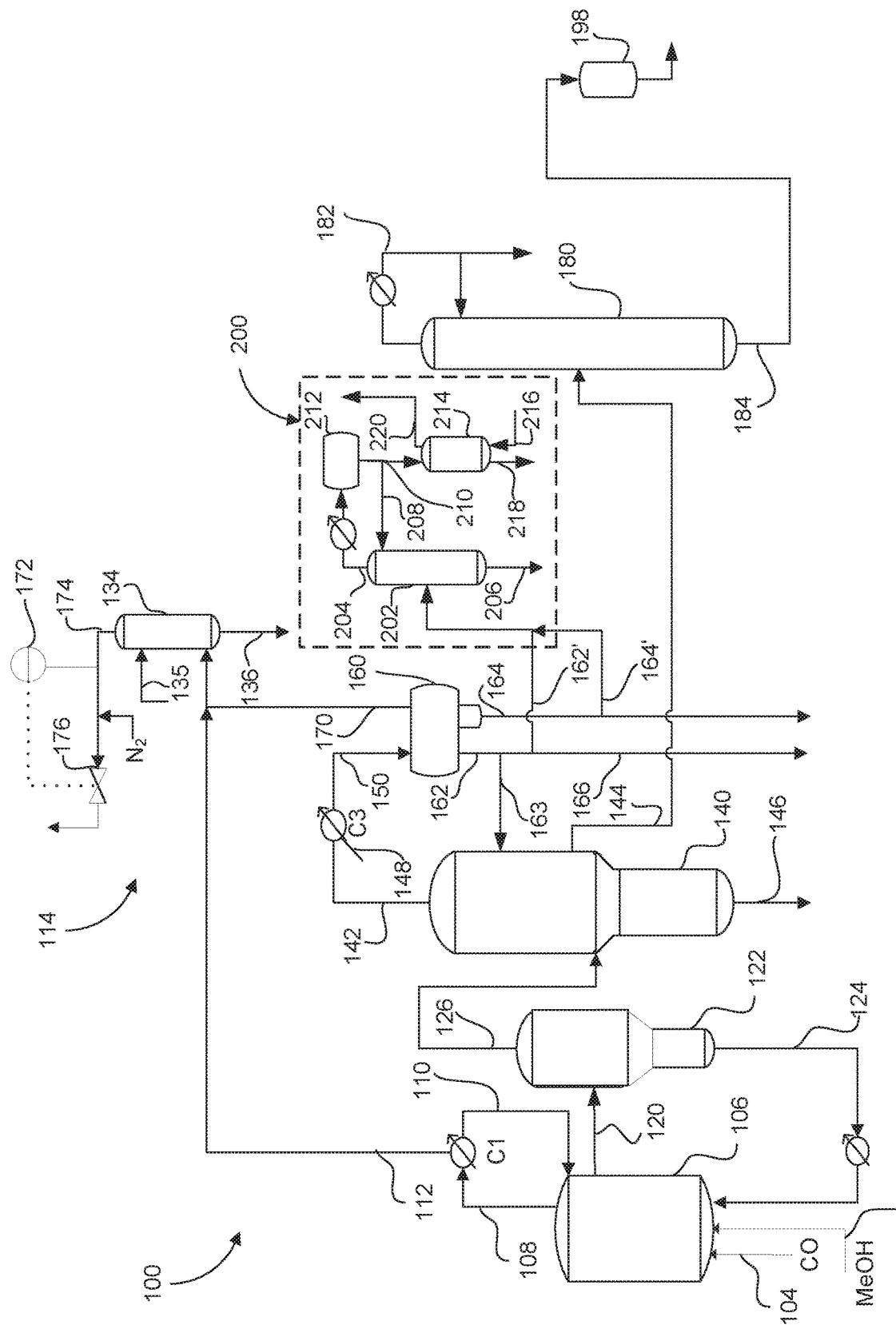
FIG. 2 illustrates another process for producing acetic acid having a valve on the vapor discharge to control the pressure of the flash vessel and first column, in accordance with embodiments of the present invention.

Some embodiments of the present invention will be described with reference to the carbonylation reaction to produce acetic acid. An exemplary flow diagram 100 of the reaction and acetic acid recovery are shown in FIGS. 1 and 2. As described further below, the apparatuses used with the flow diagram 100 may include a reactor vessel, flash vessel, one or more distillation columns, decanters, ion exchange resin beds, absorption systems, and/or extractors, along with the associated heat exchanges, pumps, condensers, receivers, reboilers, valves, pipes and process controllers. The configuration of the flow diagram 100 is not particularly limiting and can encompass a range of various configurations as shown in FIGS. 1 and 2. For the purposes of this disclosure, the pressure is controlled between the flash vessel and a distillation column that receives the fed from the flash vessel, e.g., the first distillation column. This first distillation column may be referred to herein as the light ends column and is used to remove low boiling point components from the vapor product stream.

The reactor 106 is a unit for performing the homogenous carbonylation reaction step in the liquid phase. The reaction step is for carbonylating methanol to produce acetic acid in a continuous manner. The starting materials in the reaction are liquid methanol and gaseous carbon monoxide. As shown, methanol-containing feed stream 102 and carbon monoxide-containing feed stream 104 are directed to reactor 106, in which the carbonylation reaction occurs to form acetic acid. Although not shown, a flow transmitter may be present on the both feed streams to control and/or monitor the flow of each respective stream. In particular, controlling and/or monitoring the mass flow of the methanol-containing feed stream 102 is useful for determining the efficiency of the process. As the mass flow changes, the pressure in the flash vessel and/or light ends column may be adjusted.

Methanol-containing feed stream 102 may comprise at least one member selected from the group consisting of methanol, dimethyl ether, and methyl acetate. Methanol-containing feed stream 102 may be derived in part from a fresh feed from a reservoir tank (not shown), a recycled feed from the system, or a combination of fresh and recycles feeds. At least some of the methanol and/or reactive derivatives thereof will be converted to, and hence present as, methyl acetate in the liquid medium by esterification reaction with acetic acid.

Carbon monoxide-containing feed stream 104 may comprise primarily carbon monoxide of greater than or equal to 95 vol. %, e.g., greater than or equal to 97 vol. % or greater than or equal to 99 vol. %. In some embodiments, minor impurities such as hydrogen, carbon dioxide, oxygen, and/or nitrogen may be present in amount of less than 5 vol. %, e.g., less than 3 vol. % or less than 1 vol. %. These minor impurities may also be generated by various side reactions under operating conditions.

The carbon monoxide partial pressure, at an absolute pressure, in the reactor may vary widely but is typically from 2 to 30 atm (absolute pressure), e.g., from 3 to 18 atm or from 6 to 15 atm. The hydrogen, which may be generated in the reaction or may be supplied as needed, increases the catalytic activity but can also result in formation of byproducts, including acetaldehyde. The hydrogen partial pressure, at an absolute pressure, in the reactor is typically from 0.05 to 5 atm, e.g., from 0.25 to 2 atm or from 0.3 to 1.8 atm. Because of the partial pressure of byproducts, which is typically less than 1 atm, and the vapor pressure of the contained liquids, the total reactor internal pressure may range from 15 to 40 atm (absolute pressure). In some embodiments, the internal pressure of the reactor 106 may be controlled by withdrawing a gaseous purge stream 108. In some embodiments, the internal pressure may be constant or substantially constant, which refers to minor variations in pressure over a continuous process that does not impact production rates. By carrying out the reaction under such pressure conditions, acetic acid is efficiently produced while inhibiting various byproducts and side reactions.

Typical carbonylation reaction temperatures may be greater than or equal to 150° C., e.g., greater than or equal to 175° C. or greater than or equal to 185° C. In terms of ranges, the carbonylation reaction temperature may be from 150° C. to 250° C., e.g., from 175° C. to 230° C. or from 185° C. to 205° C. The carbonylation reaction is exothermic and temperature of the reactor may be regulated by a variety of methods. For purposes of the present disclosure, any suitable cooling may be used to regulate the temperature of the reactor. U.S. Pat. No. 5,374,774 describes a cooling unit in the recycle line for the reactor. A pump around loop may be used to generate additional heat for the production of steam while regulating the temperature of the carbonylation reactor, which is further described in U.S. Pat. No. 8,530,696. In some embodiments, the temperature of the reactor may be controlled by condensing a portion of the flash overhead that is returned to the reactor, which is further described in U.S. Pat. No. 8,957,248.

The production rate of acetic acid may be from 5 to 50 mol/L·h, e.g., from 10 to 40 mol/L·h, or from 15 to 35 mol/L·h. "Greater production rates" generally refers to operating above 20 mol/L·h. In some embodiments, acetic acid is efficiently produced at greater rates when the flash vessel and light ends column are controlled to operate at low pressure and have a small pressure differential.

Carbon monoxide is introduced at a rate sufficient to maintain the desired internal reactor pressure. In some embodiments, carbon monoxide is continuously introduced through stream 104 into the carbonylation reactor 106, desirably below the agitator, which may be used to stir the contents, and thoroughly disperse the carbon monoxide throughout the liquid reaction medium. Other methods of agitating the reaction medium may be employed, such as a vessel with an eductor or pump-around mixing, or bubble-column type vessel, with or without an agitator.

The material of the carbonylation reactor and its internals is not particularly limited and may be a metal, a ceramic, a glass, or combinations thereof. For example, the material may include zirconium-based materials and alloys that tend to have high corrosion resistance, but may also include iron-based alloys (stainless steel), nickel-base alloys (HASTELLOY™ or INCONEL™), titanium-based materials and alloys, or aluminum-based materials or alloys.

Under continuous production conditions, various gas-phase components may be formed or evolved from the liquid reaction. The gas-phase component can include carbon monoxide, hydrogen, methane, carbon dioxide, acetic acid, methyl acetate, methyl iodide, hydrogen iodide, acetaldehyde, dimethyl ether, and water. In some embodiments, the gaseous purge stream 108 contains low amounts of hydrogen iodide of less than or equal to 1 vol. %, e.g., less than or equal to 0.9 vol. %, less than or equal to 0.8 vol. %, less than or equal to 0.7 vol. %, or less than or equal to 0.5 vol. %. To prevent an undesirable buildup of various gas-phase components, a gaseous purge stream 108 is drawn from the upper portion of the reactor 106.

Venting gaseous purge stream 108 from the reactor 106 further reduces the buildup of gaseous byproducts and maintains a set carbon monoxide partial pressure at a given total reactor pressure. To prevent loss of useful components, the gaseous purge stream 108 may be cooled by heat exchange with a cooling medium in one or more condensers C1 to partially condense any condensable liquids present as vapors in the gaseous purge stream into a condensate portion 110 and a gaseous portion 112. Condensate portion 110 typically includes useful liquid products, such as acetic acid, methyl acetate, methyl iodide, acetaldehyde, dimethyl ether, and water, and is returned to the reactor 106. Although the gaseous portion may be flared, the gaseous portion 112 typically includes sufficient amounts of carbon monoxide, hydrogen, methane, carbon dioxide and minor amounts of iodides such as methyl iodide or hydrogen iodide to make further recovery desirable.

The gaseous portion 112 may be further processed in an absorption system 114, such as a scrubber system or a pressure swing absorption tower. As shown in FIG. 1, the gaseous portion 112 is introduced to a high pressure absorber tower 116 to recover any remaining useful components, such as carbon monoxide, methyl acetate and/or methyl iodide in line 117. Tower 116 operates at a high pressure of greater than or equal to 0.7 atm (gauge), e.g., greater than or equal to 1 atm or greater than or equal to 2 atm. The separation and recovery in the high pressure absorber tower 116 may be performed according to a wet process using an absorbing liquid 118, such as water, acetic acid, methyl acetate or methanol. A crude acetic acid product may be used as the absorbing liquid 118. This wet process removes substantially all of the remaining methyl iodide present in the gaseous portion 112 and recovers methyl iodide by absorption into the absorbing liquid. A vent purge 119 may be removed from the top. The tower may be constructed of a corrosion resistant material, such as zirconium alloy.

Returning to the reactor 106, the catalyst in the reaction medium plays the role of promoting the methanol carbonylation reaction. In commercial production, the metal catalyst does not activate methanol directly, so a more reactive methyl substrate (reactant) must be generated in situ. An iodide promoter, such as hydrogen iodide, converts the methanol into methyl iodide. However, since most of the reaction medium is acetic acid, the methanol is esterified to methyl acetate, which is activated by hydrogen iodide into methyl iodide.

The components of the reaction medium are maintained within defined limits to ensure sufficient production of acetic acid and utilization of reactants, while limiting the production of byproducts. The following amounts are based on the total weight of the liquid phase of the reaction medium. In a continuous process, the amounts of components are maintained within the ranges provided and fluctuations within these ranges are anticipated. One of ordinary skill would readily understand how to control the process to maintain the amounts of components in the reaction medium.

The reaction medium includes a concentration of the Group VIII metal catalyst, e.g., cobalt, rhodium, iridium, or combinations thereof, in an amount from 200 to 3000 wppm based on the metal in the reaction medium, e.g., from 800 to 3000 wppm, or from 900 to 1500 wppm.

Water in the reaction medium is a useful component for forming acetic acid according to the methanol carbonylation reaction mechanism, and further dissolves soluble components in the reaction medium. The concentration of water in the reaction medium is maintained to be less than or equal to 14 wt. %, e.g., from 0.1 wt. % to 14 wt. %, from 0.2 wt. % to 10 wt. % or from 0.25 wt. % to 5 wt. %. To control the water concentration, water may be continuously fed to the carbonylation reactor 106, including through the recycles lines, at a predetermined flow rate. In some embodiments, the reaction is conducted under low water conditions and the reaction medium contains water in an amount from 0.1 to 4.1 wt. %, e.g., from 0.1 to 3.1 wt. % or from 0.5 to 2.8 wt. %. In another embodiment, the reaction is conducted with water in an amount of less than or equal to 2 wt. % water, e.g., from 0.1 to 2 wt. %, or from 0.1 to 1.9 wt. %.

The promoter in the reaction medium may be an iodide to assist the activity of the catalyst. Non-limiting examples of the iodide as the promoter include methyl iodide, an ionic iodide, and combinations thereof. The concentration of methyl iodide in the reaction medium is maintained to be from 1 to 25 wt. %, e.g., from 5 to 20 wt. %, or from 4 to 13.9 wt. %. The ionic iodide can stabilize the metal catalyst and inhibit side reactions. Non-limiting examples of the ionic iodide include lithium iodide, sodium iodide, and potassium iodide. The concentration of iodide salt, e.g., lithium iodide, in the reaction medium is maintained to be from 1 to 25 wt. %, e.g., from 2 to 20 wt. %, or from 3 to 20 wt. %. The iodide salt may be formed in situ, for example, by adding lithium acetate, lithium carbonate, lithium hydroxide or other lithium salts of anions compatible with the reaction medium. In some embodiments, the process may maintain a concentration of lithium acetate in the reaction medium from 0.3 to 0.7 wt. %, e.g., from 0.3 to 0.6 wt. %.

It will be generally recognized that it is the concentration of iodide ion in the catalyst system that is important and not the cation associated with the iodide, and that at a given molar concentration of iodide, the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable.

As described above, the methyl acetate may be formed by the reaction between acetic acid and methanol. The concentration of methyl acetate in the reaction medium is maintained to be from 0.5 to 30 wt. %, e.g., from 0.5 to 20 wt. %, from 0.6 to 9 wt. %, or from 0.6 to 4.1 wt. %.

Acetic acid is the main product of the reaction and the concentration of acetic acid in the reaction medium, which also functions as solvent, is generally in amount of greater than or equal to 30 wt. %, e.g., greater than or equal to 40 wt. % or greater than or equal to 50 wt. %. The acetic acid in the reaction medium includes acetic acid previously charged into the reactor upon start-up.

In addition to the acetic acid product, various byproducts may also be generated in the reaction medium. Non-limiting examples of the byproducts also include hydrogen, methane, carbon dioxide, formic acid, hydrogen iodide, acetic anhydride, acetaldehyde, crotonaldehyde, 2-ethyl crotonaldehyde, dimethyl ether, propionic acid, and alkyl iodides such as ethyl iodide, hexyl iodide, and decyl iodide. Hydrogen iodide is formed via the reaction mechanism of the methanol carbonylation reaction when the catalyst alone or in combination with the promoter as described above is used. The reaction medium may have an acetaldehyde concentration ranging from 0 to 1800 wppm of the total reaction medium, e.g., from 200 to 1600 wppm, or from 350 to 1000 wppm. The reaction medium may have a hydrogen iodide concentration ranging from 50 to 5000 wppm of the total reaction medium, e.g., from 100 to 3000 wppm, or from 200 to 2000 wppm. In some embodiments, the reaction medium may also include acetic anhydride. The reaction medium may have an acetic anhydride concentration ranging from 0 to 5000 ppm of the total reaction medium, e.g., from 0.01 to 3000 ppm, or from 0.1 to 1000 ppm.

Byproducts may be controlled by regulating the reaction medium and, in addition, the byproducts may be removed by separation process as described further herein. For example, as described in U.S. Pat. No. 8,017,802, formic acid may be controlled by the water content in the reactor resulting in a formic acid content in the acetic acid product that is less than 160 wppm, e.g., less than 140 wppm, or less than 100 wppm. Separation of byproducts may be limited by the associated costs. When the byproducts are not removed, especially higher boiling point components, the components can concentrate in the acetic acid product. Thus, it is useful to limit the production of byproducts in the reactor to reduce the need for separation. For example, in some embodiments, the propionic acid concentration in the acetic acid product may further be maintained below 250 wppm by maintaining the ethyl iodide concentration in the reaction medium at less than or equal to 750 wppm, e.g., less than or equal to 350 wppm, without removing propionic acid from the acetic acid product.

The various ranges for the maintaining the components for higher production rates are as follows. In some embodiments, the production rate of acetic acid is from 15 mol/L·h to 35 mol/L·h, the concentration of the rhodium catalyst in the reaction medium is maintained from 900 to 1500 wppm, the concentration of water is maintained from 0.5 to 2.8 wt. %, the concentration of methyl iodide is maintained from 4 to 13 wt. %, the concentration of lithium iodide is maintained from 3 to 20 wt. %, the concentration of lithium acetate is maintained from 0.35 to 0.55 wt. %, the concentration of methyl acetate is maintained from 2 to 3.5 wt. %, and the concentration of hydrogen iodide is maintained at less than or equal to 0.5 wt. %. The balance of the reaction medium is acetic acid.

Flash Vessel

In steady state operations, the reaction medium is continuously withdrawn from the reactor 106 as stream 120 at a rate sufficient to maintain a constant level therein. For purposes of the present invention the flash flow or second mass flow rate refers to the withdrawn reaction medium from the reactor. To obtain the acetic acid product, the withdrawn reaction medium in stream 120 is fed to the subsequent downstream flash vessel 122. In some embodiments, a converter reactor (not shown) or a pipe reactor (not shown) can be employed between the reactor and flash vessel. A pipe reactor is described in U.S. Pat. No. 5,672,744 and is used to react the dissolved carbon monoxide in the reaction medium. Chinese Patent No. CN1043525C describes a converter reactor to allow the reaction to proceed to a greater extent prior to subsequent flashing. The converter reactor produces a vent stream comprising gaseous components which are typically scrubbed with a compatible solvent to recover components such as methyl iodide and methyl acetate. As described herein, the gaseous purge stream 108 from the reactor 106 and converter can be combined or scrubbed separately and are typically scrubbed with either acetic acid, methanol or mixtures of acetic acid and methanol, to prevent loss of low boiling components such as methyl iodide from the process.

The separation vessels are maintained at a pressure considerably lower than the pressure in the carbonylation reactor. Those skilled in the thermodynamic arts are aware that this pressure reduction is accompanied by flashing of the more volatile components of the liquid reaction product solution. In this way, the carbonylation product, which has a higher vapor pressure than the catalyst, is removed as a vapor leaving behind the catalytic agent in the unflashed liquid carbonylation product solution. This separation is desirable to obtain a fraction of the product as a vapor and is separated from the Group VIII metal catalyst which remains in the liquid phase. Thus, the high cost catalyst may be recycled back into the reactor, while the vapor product is provided for further purification in a form free of catalytic contamination.

Flash vessel 122 performs a flash evaporation or distillation step, referred to herein as flashing or evaporating, to return the residual liquid catalyst 124 to the reactor 106 and separate a vapor product stream 126 comprising acetic acid for further processing. In some embodiments, the flashing may be performed by decompressing the reaction medium in stream 120 with or without heating. Stream 120 may be tangentially fed through one or more feed ports as shown in U.S. Pat. No. 6,599,348. To direct the liquid portion downwards, a splash plate may be used in each of the feed ports. In some embodiments, the flashing may be carried out to produce a vapor temperature from 100° C. to 260° C., and a residual liquid temperature from 80° C. to 200° C. The internal pressure (gauge) of the flash vessel 122 may be from 0.5 atm to 5 atm, e.g., from 0.5 atm to 3.5 atm, 0.5 to 2.5 atm, or from 0.5 to 1.5 atm.

In some embodiments, the internal pressure of the flash vessel 122 is greater than the internal pressure of the first column 140. Even though flash vessel 122 operates at a greater pressure, the pressure differential should be small between the flash vessel 122 and first column 140. The present inventors have found that a small pressure differential may be obtained by controlling the vent of the vapor discharge. In some embodiments, the pressure differential is less than or equal to 0.5 atm, e.g., less than or equal to 0.4 atm, less than or equal to 0.3, less than or equal to 0.25 atm, or less than or equal to 0.2 atm.

Further, it is desirable to efficiently produce acetic acid by increasing the pressure in the flash vessel 122 as the production rates increase and to reduce the pressure where there is a scale-back in production rates. When the pressure remains unchanged with falling production rates, the amount of liquid catalyst recycle is reduced and the flow must be increased. Also, the carbon monoxide entrainment in the vapor product increases and results in a greater loss of raw materials. Both of these are undesirable conditions that lead to process inefficiencies.

As described by the embodiments herein, the flash vessel 122 operates on the back pressure established by controlling the vapor discharge on a tower in the absorption system 114. This provides several advantages, including the ability to operate at the lowest possible pressure for a given production rate. In addition, this reduces the pressure differential between the flash vessel 122 and subsequent downstream vessels, such as the light ends column 140. Further, no dedicated pressure control sensor is needed for the flash vessel or vapor line allowing the flash vessel to operate at an efficient pressure for producing acetic acid at a given production rate. This further simplifies the control scheme and reduces operating costs.

The mass ratio of the vapor product stream 126 to the residual liquid catalyst stream 124, which are separated from each other, may be from 10:90 to 50:50, e.g., from 20:80 to 40:60. The vapor product stream 126 comprises acetic acid, as well as methyl iodide, methyl acetate, water, permanganate reducing compounds (PRC's), and other byproducts or impurities. Dissolved gases in the reaction medium that enter the flash vessel are concentrated into the stream 126. The dissolved gases comprise a portion of the carbon monoxide and may also contain gaseous byproducts such as methane, hydrogen, and carbon dioxide. In some embodiments, a mist eliminator may be employed near the vapor outlet to coalesce liquid droplets. An optional scrubbing section (not shown) may further be employed in the vapor outlet of the flash vessel to reduce entrainment from metallic catalysts or other metallic components into the vapor stream. A wash liquid may be introduced into the optional scrubbing section.

Vapor product stream 126 comprises acetic acid, methyl iodide, methyl acetate, water, acetaldehyde, and hydrogen iodide. The flash vessel 122 may be operated under conditions sufficient to vaporize at least 80% of the methyl iodide and methyl acetate, based on the total reaction medium, into the vapor product stream 126. In some embodiments, vapor product stream 126 comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor product stream. In another embodiment, vapor product stream 126 comprises acetic acid in an amount from 45 to 75 wt. %, methyl iodide in an amount from 24 to less than or equal to 36 wt. %, methyl acetate in an amount of less than or equal to 9 wt. %, and water in an amount of less than or equal to 15 wt. %, based on the total weight of the vapor product stream. More preferably, vapor product stream 126 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, vapor product stream 126 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream 126 may be in an amount from 0.005 to 1 wt. %, based on the total weight of the vapor product, e.g., from 0.01 to 0.8 wt. %, or from 0.01 to 0.7 wt. %. Vapor product stream 126 may comprise hydrogen iodide in an amount less than or equal to 1 wt. %, based on the total weight of the vapor product stream, e.g., less than or equal to 0.5 wt. %, or less than or equal to 0.1 wt. %. The propionic acid, acetic anhydride, or formic acid, if present, may be present in amounts in vapor product stream 126 in a reduced amount of less than 1 wt. %, e.g., less than 0.5 wt. %.

In some embodiments, the entire vapor product stream 126 is directed to the light ends column 140 as a vapor stream. This provides the heat to separate the components in the light ends column 140. In some embodiments, there is provided a condenser C2 that cools and partially condenses a portion 128 of the vapor product stream 126 to efficiently remove heat generated in the carbonylation reaction. The condensed portion 130 formed by cooling may be passed through a heat exchanger prior to being transferred to the reactor 106. In other embodiments, the condensed portion 130 may be forwarded to light ends column 140 to debottleneck and increase capacity. The non-condensable gaseous portion 132 from cooling in the condenser C2 may be directed to the low pressure absorption tower 134 in absorption system 114.

To handle the liquid recycle stream 124 in a manner that maintains flow rates, prevents equipment damage, and provides sufficient control, a vortex breaker (not shown) may be used near the liquid outlet of the flash vessel 122. Liquid recycle stream 124 comprises acetic acid, the metal catalyst, corrosion metals, as well as other compounds that remain without volatilization in the flashing step. In some embodiments, liquid recycle stream comprises acetic acid in an amount from 60 to 90 wt. %, metal catalyst in an amount from 0.01 to 0.5 wt. %, corrosion metals (e.g., nickel, iron and chromium) in a total amount from 10 to 2500 wppm, lithium iodide in an amount from 5 to 20 wt. %, methyl iodide in an amount from 0.5 to 5 wt. %, methyl acetate in an amount from 0.1 to 5 wt. %, water in an amount from 0.1 to 8 wt. %, acetaldehyde in an amount of less than or equal to 1 wt. % (e.g., from 0.0001 to 1 wt. % acetaldehyde), and hydrogen iodide in an amount of less than or equal to 0.5 wt. % (e.g., from 0.0001 to 0.5 wt. % hydrogen iodide).

The residual liquid catalyst may be predominantly acetic acid containing the rhodium and the iodide salt along with lesser quantities of methyl acetate, methyl iodide, lithium acetate and water and is recycled to the reactor, as discussed above. Prior to returning residual liquid catalyst to the reactor, a slip stream may pass through a corrosion metal removal bed, such as an ion exchange bed, to remove any entrained corrosion metals, such as nickel, iron, chromium, and molybdenum, as described in U.S. Pat. No. 5,731,252, which is incorporated herein by reference in its entirety. Entrained corrosion metals if not controlled can lead to decrease in catalytic activity and fouling of the equipment. Also, the corrosion metal removal bed may be used to remove nitrogen compounds, such as amines, as described in U.S. Pat. No. 8,697,908, which is incorporated herein by reference in its entirety.

In some embodiments, to prevent deactivation of the catalyst in the flash vessel, carbon monoxide may be introduced in the base of the flash vessel. More specifically, the carbon monoxide is fed into the liquid in the base of the flash vessel that contains the metallic catalyst. Catalyst deactivation and loss, especially for rhodium catalyst, is generally believed due to carbon monoxide-depleted or low pressure environments in the carbonylation system as are typically experienced in the flash vessel.

The flashing may be performed using a two-stage flash, where the absolute internal pressure in the first flash vessel may be in the range from 1 to 10 atm and the pressure in the second flash vessel may suitably be in the range from 0 to 5 atm. The pressure in both stages operates on the backpressure from the absorption system. In some embodiments, prior to entering the flash vessel 122, the reaction medium may be fed to a pre-flash vessel (not shown) operating at an intermediate pressure between the operating pressures of the carbonylation reactor and a subsequent flash vessel, thereby retaining most of the product acetic acid in solution, while flashing off methyl iodide and methyl acetate. In this embodiment, the methyl iodide and methyl acetate flashed off from the pre-flash vessel may be fed to a condenser or may be sent directly to a low-pressure absorber, thereby reducing the load on a downstream distillation column.

Further details are described in U.S. Pat. No. 8,168,822, the entire contents and disclosures of which are hereby incorporated by reference.

Light Ends Column

For purposes of the present invention, the downstream distillation of the vapor product and recovery of acetic acid is not particularly limited. For pressure control, the distillation column downstream of the flash vessel also operates on the backpressure established by the vent on the absorbing system. Thus, no separate dedicated pressure control is needed on the downstream distillation equipment. This allows a minimal pressure differential between the flash vessel and distillation column that is desirable when producing acetic acid at greater production rates. As described herein, the downstream column will be described as a light ends column.

As shown in FIG. 1, vapor product stream 126 is continuously introduced into a first column 140, also referred to as a light ends column. Distillation yields a low-boiling overhead stream 142, an acetic acid product that preferably is removed via a side stream 144, and a residue stream 146, which may be recycled to the reactor. In some embodiments, side stream 144 may pass through a side condenser to further reduce impurities. In other embodiments, a vapor portion (not shown) drawn from above the side stream may be condensed to further increase capacity in first column 140 as described in U.S. Pat. No. 7,989,659.

Residue stream 146 contains a larger amount of components having a higher boiling point than that of acetic acid, and contains more of these components than low-boiling overhead stream 142 or side stream 144. In addition, residue stream 146 may also contain entrained catalyst. The components of residue stream 146 also include acetic acid, methanol, methyl acetate, and/or water. Residue stream 146 is recycled to flash vessel 122 or reactor 106. In some embodiments, the continuous process may operate without residue stream 146.

First column 140 may be a plate column, packed column, or a combination thereof. In some embodiments, distillation column 140 is a plate column typically having from 5 to 80 theoretical plates, e.g., from 5 to 50 theoretical plates. The column top pressure and bottom pressure of first column 140 operates on the established backpressure from the vent of vapor discharge 174 in absorption system 114. In addition, this backpressure controls the top pressure (gauge) in first column 140 within the range from 0.5 to 4 atm, e.g., from 0.8 to 3 atm, or from 1 to 2.5 atm. As discussed above, the top pressure in the first column 140 is less than the pressure of flash vessel 122, but the pressure differential is small. The pressures at the bottom of first column 140 are typically higher and may range from 0.6 to 4.5 atm, e.g., from 0.9 to 3.5 atm, or from 1.1 to 3 atm. The bottom pressure is also controlled by the backpressure from the vent of vapor discharge 174 in absorption system 114.

In some embodiments, first column 140 operates with a column top temperature that is set at a temperature which is lower than the boiling temperature of acetic acid at the column top pressure, such as from 80° C. to 150° C., e.g., 90° C. to 130° C. The bottom temperature may range from 100° C. to 180° C., e.g., from 120° C. to 165° C. or from 125° C. to 160° C. In some embodiments, the heat for the distillation is primarily provided by vapor product stream 126. In some embodiments, when supplemental heat is required, a reboiler may provide further heat for the distillation in first column 140.

In some embodiments, low-boiling overhead stream 142 comprises water, methyl acetate, methyl iodide, hydrogen iodide, acetaldehyde, dimethyl ether, and other light carbonyl impurities, as well as acetic acid. The amount of water in low-boiling overhead stream 142 is generally greater than or equal to 5 wt. %. Low-boiling overhead stream 142 is continuously passed through one or more condensers C3, which may be supplied with cooling water via line 148 at a temperature of less than or equal to 60° C., e.g., from 20° C. to 60° C. or from 20° C. to 40° C., to partially condense low-boiling overhead stream 142. The condensate and gaseous components from condenser C3 pass into decanter 160 through line 150. Decanter 160 may be an overhead receiver for collecting the liquid portion from C3, having a coalescing member, that allows for phase separation. In some embodiments, the condensate and gaseous components are directed in separate lines and in other embodiments, both components may be passed together in a shared line. In some embodiments, the condensate in line 150 may be further condensed in one or more optional condensers operating at successively lower temperatures. After each subsequent condensing step, both the condensate and gaseous components pass together until they are separated in decanter 160.

In some embodiments, the average residence time of the condensed components in decanter 160 is greater than or equal to 1 minute, e.g., greater than or equal to 3 minutes, greater than or equal to 5 minutes, greater than or equal to 10 minutes. In some embodiments, the average residence time of the condensed components in decanter 160 is less than or equal to 60 minutes, e.g., less than or equal to 45 minutes, less than or equal to 30 minutes, or less than or equal to 25 minutes. The condensate components introduced into decanter 160 are separated into an aqueous phase 162 and an organic phase 164. Aqueous phase 162 primarily includes water typically with methyl acetate, acetic acid, hydrogen iodide, acetaldehyde, dimethyl ether, methanol, and lesser amounts of methyl iodide. Methyl iodide concentrates in organic phase 164 which further includes methyl acetate, acetaldehyde, dimethyl ether, hydrogen iodide, methanol, and lesser amounts of water and acetic acid. In some embodiments, the acetaldehyde concentration in aqueous phase 162 is larger, based on wt. %, than organic phase 164. Although the specific compositions of aqueous phase 162 may vary widely, some exemplary compositions are provided below in Table 1.

TABLE 1

Exemplary Aqueous Phase from Light Ends Overhead

|  | conc. (Wt. %) | conc. (Wt. %) | conc. (Wt. %) |
| --- | --- | --- | --- |
| Water | 40-80 | 50-75 | 70-75 |
| Methyl Acetate | 1-50 | 1-25 | 1-15 |
| Acetic Acid | 1-40 | 1-25 | 5-15 |
| PRC's (AcH) | <5 | <3 | <1 |
| Methyl Iodide | <10 | <5 | <3 |
| Hydrogen Iodide | <1 | <0.5 | 0.001-0.5 |

In some embodiments, a portion of aqueous phase 162 may be refluxed through line 163 into first column 140. The reflux ratio (the mass flow rate of the reflux divided by the total mass flow exiting the top of column 140, including both organic phase 164, which may or may not be fully recycled, and aqueous phase 162) of aqueous phase 162 via line 163 to first column 140 is from 0.05 to 0.4, e.g., from 0.1 to 0.35, or from 0.15 to 0.3. In some embodiments, another portion of aqueous phase 162 may be returned to reactor 106 via line 166.

Organic phase 164, which is primarily methyl iodide, is recycled into the reactor 106. In some embodiments, a portion of organic phase 164 may be refluxed with the aqueous phase 162 to the first column 140. The specific gravity of organic phase 164 may be from 1.3 to 2, e.g., from 1.5 to 1.8, from 1.5 to 1.75 or from 1.55 to 1.7. As described in U.S. Pat. No. 6,677,480, the measured specific gravity in organic phase 164 may correlate to the methyl acetate concentration in the reaction medium. As specific gravity decreases, the methyl acetate concentration in the reaction medium increases. In some embodiments, overhead decanter 160 is arranged and constructed to maintain a low interface level to prevent an excess hold up of methyl iodide. Although the specific compositions of organic phase 164 may vary widely, some exemplary compositions are provided below in Table 2.

TABLE 2

Exemplary Organic Phase from Light Ends Overhead

|  | conc. (Wt. %) | conc. (Wt. %) | conc. (Wt. %) |
| --- | --- | --- | --- |
| Water | <3 | 0.05-1 | 0.01-1 |
| Methyl Acetate | 0.1-25 | 0.5-20 | 0.7-15 |
| Acetic Acid | 0.1-10 | 0.5-10 | 0.7-10 |
| PRC's (AcH) | <5 | <3 | 0.05-0.5 |
| Methyl Iodide | 60-98 | 60-95 | 80-90 |
| Hydrogen Iodide | <1 | <0.5 | 0.001-0.5 |

The gaseous components from condenser C3 introduced into decanter 160 are vented into gaseous stream 170. The gaseous components may include carbon monoxide, carbon dioxide, hydrogen, nitrogen, oxygen, methane, acetic acid, methyl acetate, methanol, water, acetaldehyde, dimethyl ether, methyl iodide, hydrogen iodide, and combinations thereof from both flash vessel 122 and first column 140.

In some embodiments, vented gaseous stream 170 passes through a condenser (not shown) that is supplied with chilled liquid at a temperature from −10° C. to 20° C., e.g., from 0° C. to 20° C. The condensate, which mainly contains condensable components, is returned to the decanter, while gaseous component continues to a low pressure absorber tower 134. Methyl iodide, hydrogen iodide, and other condensable gaseous components in the gaseous components are absorbed by an absorbing liquid (absorbent) 135 in low pressure absorber tower 134.

Vapor Discharge for Backpressure

Absorber tower 134 operates at a pressure that is less than high pressure absorber tower 116. In some embodiments, the contact with the absorbing liquid in absorber tower 134 is carried out at a pressure from 0 to 3 atm (gauge), e.g., from 0.5 to 2.5 atm (gauge). In the low pressure absorber tower 134, the hydrogen iodide in absorbing liquid 135 reacts with methanol or methyl acetate to form methyl iodide. In some embodiments, the absorbing liquid 135 may be chilled to a temperature from 0° C. to 40° C., e.g., from 15° C. to 35° C. or from 20° C. to 30° C. Such a liquid containing useful components such as the methyl iodide is introduced or recycled from the low pressure absorber tower 134 through recycling line 136 into reactor 106 or flash vessel 122, to be reused. Recycling line 136 from the low pressure absorber tower 134 is combined with line 117 from the high pressure absorbing tower 134 and are fed to stripper column 138 to recover the solvent in line 137 that may be reused for absorber towers 116 and 134. The recycled portion is obtained from line 139 and fed to reactor 106 or flash vessel 122 as desired.

To establish backpressure for flash vessel 122 and first column 140, there is a pressure control unit 172 at the top of the low pressure absorber tower 134 according to various embodiments of the present invention. In some embodiments, pressure control unit 172 detects the pressure of the vapor discharge 174 from low pressure absorber 134. A predetermined threshold value may be established to control the pressure through the control valve 176. For purposes of the present invention, any suitable valve may be used, including but not limited to diaphragm, needle, ball, gate, or check valves. In some embodiments, the predetermined threshold value may be set based on the production rates of acetic acid. Control valve 176 adjusts the flow of the vent overhead to establish a backpressure for the upstream equipment, e.g., flash vessel 122 and light ends column 140. When the detected pressure is less than the predetermined threshold value, a signal is sent from pressure control unit 172 to close control valve 176 and increase backpressure. In further embodiments, an inert gas feed, such as $N_2$, may be used when the detected valve is excessively small. A small inert gas flow helps to improve the responsiveness and controllability of control valve 176.

In some embodiments, the pressure of the vapor discharge 174 is maintained to be less than both flash vessel 122 and light ends column 140. In some embodiments, pressure control unit 172 controls the pressure within the range from 0.2 to 3 atm, e.g., from 0.3 to 2.5, or from 0.4 to 2 atm. To improve efficiencies, it is more desirable to operate at the lower end of this range. As the relative flow of the methanol-containing stream 102 decreases, pressure control unit 172 may lower the pressure to provide efficient flow of vapor stream 126 between flash vessel 122 and light ends column 140. Thus, in some embodiments, there may be a flow control monitor (not shown) on methanol-containing stream 102.

Further Purification

Returning to light ends column 140, side stream 144 may comprise acetic acid in an amount from 90 to 99.5 wt. %, water in an amount from 1 to 3 wt. %, methyl iodide in an amount from 0.1 to 5 wt. %, and methyl acetate in an amount from 0.1 to 5 wt. %. As described herein, acetic acid removed via side stream 144 is preferably subjected to further purification as shown in FIG. 1, such as in a second column 180, also referred to as a dehydrating or drying column. A third column 190 may be used in some embodiments to further remove heavy impurities. In some embodiments, a portion of side stream 144 may be condensed and fed back into first column 140. The concentration of catalyst in side stream 144 is typically about one or two order of magnitudes lower than the catalyst concentration in crude vapor stream 126 coming off flash vessel 122, but side stream 144 may still contain low levels of catalyst. In further embodiments, to remove any metal entrainment in side stream 144, a portion of the side stream may be treated in a fixed bed containing a polymer having nitrogen-containing heterocyclic repeat units, such as pyridine or pyrrolidone polymer, to sequester catalyst prior to entering second column 180, as described in U.S. Pat. No. 7,902,398.

As shown in FIG. 1, side stream 144 enriched in acetic acid is continuously introduced at a controlled flow rate into second column 180. In other embodiments, side stream 144 may be used as the product and no further distillation is needed and side stream 144 may pass through an iodide bed 198 to remove iodides. In still further embodiments, side stream 144 may be fed to third column 190, thereby skipping second column 180. For purposes of the present invention, the backpressure is established on flash vessel 122 and first column 140, and additional downstream columns are not operated on the backpressure. This is due in part to those additional columns operating at a pressure higher than first column 140. The particular arrangement and configuration of separation, including these additional columns, is not limited by the embodiments of the present invention.

In some embodiments, second column 180 may include a combination of different distillation apparatuses. For example, a combination of bubble-cap column and perforated plate column may be used as well as a combination of perforated plate column and a packed column. In some embodiments, second column 180 may be a plate column having up to 80 theoretical plates, e.g., from 2 to 80, from 5 to 60, from 5 to 50, or more preferably, from 7 to 35 theoretical plates. Unlike first column 140, second column 180 may operate with a dedicated pressure control. The column top gauge pressure may be from 2 atm to 4 atm with a temperature from 130° C. to 155° C. and a higher bottom gauge pressure from 2.5 atm to 5 atm with a temperature from 150° C. to 180° C.

Second column 180 separates side stream 144 to form overhead stream 182 comprised primarily of water and product stream 184 comprised primarily of acetic acid, which may be removed at base or near base, as shown by stream 184', of second column 180. Overhead stream 182 may comprise water in an amount from 50 to 95 wt. %, e.g., from 50 to 90 wt. %, or from 50 to 75 wt. %. Methyl acetate and methyl iodide are also removed from side stream 144 and concentrated in overhead stream 182. Overhead stream 182 may be condensed and refluxed as needed to the second column, with the remainder of the overhead stream being returned to reactor 106. To prevent excess iodide build up in second column 180, a decanter may phase separate the condensed overhead stream 182 and an aqueous portion is used as the reflux.

One useful function of second column 180 is to limit the iodides in product stream 184. The iodides, if not removed up to this point, are further removed out by guard beds 198 and it is desirable to operate with low iodide content to maintain a useful lifetime for the guard beds. In some embodiments, to further limit the iodides in the product stream, at least one substance selected from the group consisting of methanol, methyl acetate, and potassium hydroxide may be fed to second column 180 or the side stream fed to second column 180. These substances are known to react particularly favorably with corrosive iodides, such as hydrogen iodides, so that the iodides can be favorably be removed in the overhead and returned to the reactor.

Product stream 184, which may be taken from the base or lower portion of second column 180, comprises the acetic acid product. Depending on the concentration of high-boiling point components, such as propionic acid or acetic anhydride, the acetic acid product may be taken from a lower portion as a side stream or bottoms stream 184 may be directed to a further purification column 190 to remove the high-boiling point components. This third column 190, which may be referred to as a heavy ends column or finishing column, is an optional purification step. In other embodiments, bottoms stream 184 may be fed directly to guard beds to remove the iodides.

Third column 190 may be a plate column having up to 120 theoretical plates, e.g., from 10 to 120, from 15 to 100, from 25 to 90, or more preferably from 30 to 80 theoretical plates. Unlike first column 140, third column 190 may operate with a dedicated pressure control. The column top gauge pressure may be from 1 to 4 atm with a temperature from 110° C. to 170° C. and a higher bottom gauge pressure from 1.1 to 5 atm with a temperature from 120° C. to 180° C.

Overhead stream 192 may be condensed and refluxed as needed to third column 190, with the remainder of overhead stream 192 being returned to reactor 106. To prevent excess iodide build up in third column 190, a decanter may phase separate condensed overhead stream 192 and an aqueous portion is used as the reflux. Bottoms stream 194 may comprise heavy components and may be processed further to recover those components or discarded as needed. Side stream 196 contains the acetic acid product and it is enriched in acetic acid as compared to product stream 184. In some embodiments, side stream 196 is further processed by passing through one or more guard beds 198.

Guard Beds

A low total iodide concentration, e.g., up to 5 wppm, e.g., up to 1 wppm, is needed for the feed to the guard bed. The use of one or more guard beds to remove residual iodide greatly improves the quality of the purified acetic acid product. Carboxylic acid streams, e.g., acetic acid streams, that are contaminated with halides and/or corrosion metals may be contacted with the ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entireties. Generally, a contaminated liquid carboxylic acid stream is contacted with the ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

In some embodiments, the ion exchange resin is a metal-exchanged ion exchange resin and may comprise at least one metal selected from the group consisting of silver, mercury, palladium and rhodium. In some embodiments, at least 1% of the strong acid exchange sites of said metal-exchanged resin are occupied by silver. In another embodiment, at least 1% of the strong acid exchange sites of said metal-exchanged resin are occupied by mercury. The process may further comprise treating the purified acetic acid product with a cationic exchange resin to recover any silver, mercury, palladium or rhodium.

The pressure during the contacting step is limited primarily by the physical strength of the resin. In some embodiments, the contacting is conducted at pressures ranging from 1 to 10 atm, e.g., from 1 to 8 atm, or from 1 to 5 atm. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In some embodiments, the contacting is conducted at a temperature ranging from 25° C. to 120° C., e.g., from 25° C. to 100° C., or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard be may be configured after a heavy ends removal column or finishing column. Preferably, the guard bed is configured in a position where the temperature acetic acid product stream is low, e.g., less than or equal to 120° C., or less than or equal to 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In some embodiments, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in some embodiments the purified acetic acid product in bottoms stream 184 is contacted with a guard bed when total iodide concentration of the purified acetic acid product is up to 5 wppm, e.g., preferably up to 1 wppm. In one exemplary embodiment, the total iodide concentration of the purified acetic acid product may be from 0.01 wppm to 5 wppm, e.g., from 0.01 wppm to 1 wppm. Concentrations of iodide above 5 wppm may require re-processing the off-spec acetic acid. Total iodide concentration includes iodide from both organic, $C_1$ to $C_{14}$ alkyl iodides, and inorganic sources, such as hydrogen iodide. A purified acetic acid composition is obtained as a result of the guard bed treatment. The purified acetic acid composition, in some embodiments, comprises less than 100 wppb iodides, e.g., less than 90 wppb, less than 50 wppb, or less than 25 wppb. In some embodiments, the purified acetic acid composition comprises less than 1000 wppb corrosion metals, e.g., less than 750 wppb, less than 500 wppb, or less than 250 wppb. For purposes of the present invention, corrosion metals include metals selected from the group consisting of nickel, iron, chromium, molybdenum and combinations thereof. In terms of ranges, the purified acetic acid composition may comprise from 0 to 100 wppb iodides, e.g., from 1 to 50 wppb; and/or from 0 to 1000 wppb corrosion metals, e.g., from 1 to 500 wppb. In other embodiments, the guard bed removes at least 25 wt. % of the iodides from the crude acetic acid product, e.g., at least 50 wt. %, or at least 75 wt. %. In some embodiments, the guard bed removes at least 25 wt. % of the corrosion metals from the crude acetic acid product, e.g., at least 50 wt. %, or at least 75 wt. %.

In another embodiment, the product stream may be contacted with cationic exchanger to remove lithium compounds. The cationic exchanger in the acid form comprises a resin of acid-form strong acid cation exchange macroreticular, macroporous or mesoporous resins. Without being bound by theory, feeding a product stream to an ion-exchange comprising lithium compounds in an amount of greater than or equal to 10 wppm results in displacement of metals in the treated product. Advantageously, this may be overcome by using a cationic exchanger upstream of the ion-exchange resin. After contacting with the cationic exchanger, the product stream may have a lithium ion concentration of less than or equal to 50 weight part per billion (wppb), e.g., less than or equal to 10 wppb, or less than or equal to 5 wppb.

Although the product stream may be contacted with an ion-exchange resin to remove iodides, it is preferred not to flash the product stream or contact with product stream with an adsorption system that contains activated carbon. Flashing the product stream is not efficient because there is not a sufficient pressure drop to recover greater than 50% of the acetic acid from the product stream. Thus, in some embodiments, a non-flashed portion of the product stream is fed to the ion-exchange bed to remove iodides.

Acetaldehyde Removal

As described above, the reaction medium may contain acetaldehyde or other permanganate reducing components (PRC). PRC's may include acetaldehyde, acetone, methyl ethyl ketone, butylaldehyde, crotonaldehyde, 2-ethyl crotonaldehyde, 2-ethyl butyraldehyde, and the aldol condensation products thereof. Acetaldehyde is difficult to separate due to the close boiling point with methyl iodide. To maintain purity levels, it is desirable to remove acetaldehyde from the process, while retaining methyl iodide. Methods for removing acetaldehyde are described in U.S. Pat. Nos. 6,143,930; 6,339,171; 7,223,883; 7,223,886; 7,855,306; 7,884,237; 8,889,904; and U.S. Pub. Nos. 2006/0011462, which are incorporated herein by reference in their entirety.

Although there are several methods for removing acetaldehyde, FIG. 1 provides a suitable option in PRC removal system 200. A portion of light phase 162' and/or heavy phase 164' may be directed to a PRC removal system 200. Typically, the acetaldehyde concentrations are larger in light phase 162, but both phases are suited for removing PRC's. Accordingly, the feed to PRC removal system 200 is fed to a distillation column 202 which separates into an overhead stream 204 containing acetaldehyde and methyl iodide and a bottom returns stream 206. Bottom returns stream 206 is enriched in methyl acetate, water and acetic acid and may be returned to the reactor 106 or flash vessel 122. Overhead stream 204 is condensed and collected in an overhead receiver 212. A first portion of the receiver 208 is used as a reflux 210 to distillation column 202 and a second portion 210 is fed to an extractor 214 along with an extraction agent 216, which is typically water. Raffinate 218 contains methyl iodide and is retained with the process by recycling to reactor 106, flash vessel 122 or decanter 160. Extractant 220, which contained the removed acetaldehyde is discharged and extraction agent 216 may be recovered as desired for reuse.

The distillation columns described herein may be conventional distillation columns, e.g., a plate column, a packed column, and others, and combinations thereof. Plate columns may include a perforated plate column, bubble-cap column, Kittel tray column, uniflux tray, or a ripple tray column. For a plate column, the theoretical number of plates is not particularly limited and depending on the species of the component to be separated, may include up to 80 plates, e.g., from 2 to 80, from 5 to 60, from 5 to 50, or more preferably from 7 to 35. The distillation column may include a combination of different distillation apparatuses. Unless excluded, a combination of bubble-cap column and perforated plate column may be used, as well as a combination of perforated plate column and a packed column.

Second Embodiment

FIG. 2 illustrates another embodiment that is similar to FIG. 1 as described above with the following differences. In FIG. 2, there is one absorbing tower 134 that receives both gaseous portion 112 from reactor 106 and gaseous stream 170 from decanter 160. Because the reactor operates at higher pressure than the flash vessel and first column, the back pressure control does not affect the pressure in the reactor. The pressure in reactor 106 may be controlled by the carbon monoxide feed or through the venting of gaseous stream 112.

Further differences are as follows. These differences are variations in the acetic acid process and the embodiments described herein may operate within such variations. In FIG. 2, the entire flow vapor stream 126 is fed forward to first column 140. Also, third column 190 is removed and product stream 184 is introduced directly to one or more guard beds 198 to remove iodides as described herein. Further changes and variations to PRC removal system 200 may also be made without affecting the pressure control of the flash vessel and light ends column.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable nickel-based alloys include those containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

At the outset, it should be noted that in the development of any such actual embodiment, numerous implementation-specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

As is evident from the figures and text presented above, a variety of embodiments are contemplated.

The present invention will be better understood in view of the following non-limiting examples.

Examples

Table 3 contains the results of Examples 1-4 based on data obtained from a commercial unit. The purpose of the examples is to illustrate the benefit of adjusting the pressure of the light ends absorber in response to production rate changes.

Each of the examples operated under similar conditions. In the reactor, the reaction medium contained water in an amount from 1-3 wt. %, methyl iodide in an amount from 10-13 wt. %, methyl acetate in an amount from 1-5 wt. %, lithium iodide in an amount from 8-15 wt. % and the balance being acetic acid. The catalyst was a rhodium catalyst at a level loading from 900 to 1100 wppm. The reaction was carried out at a temperature of approximately 198° C. to 205° C.

The relative methanol mass flow was varied in each example. The reaction medium was withdrawn from a reactor and introduced to a flash vessel that separated a vapor stream and catalyst liquid recycle. The vapor stream was separated in the light ends column and a vent stream from the overhead of the light ends column was directed to an absorber system. The vapor discharge on the absorber system established the backpressure for the flash vessel and light ends column. Pressure was controlled by manipulation of a valve in the vent line from the overhead of the absorber in order to maintain a desired setpoint pressure which was measured by a pressure measuring device located in the absorber overhead line upstream of the pressure control valve.

Example 1 is the unit operating at full production rate. In this example, the vapor discharge of the absorber tower is controlled at a pressure of 1.85 atm (gauge) and the light ends column and flash vessel pressures are determined by the pressure drop through the system. Table 3 includes the flashing flow of the reaction medium from the reactor to the flash vessel as well as the ratio of the flashing flow to the production rate which is represented by the MeOH feed flow rate.

Example 2 shows a condition in which the plant is operated at less than full production rate but the absorber control pressure is not changed. In Example 2, the ratio of flash flow to MeOH feed flow is clearly higher. This results in additional operating cost per unit of production due to the higher circulation rate of catalyst per unit of product and, also, greater raw material losses per unit of production due to the loss of dissolved and entrained CO contained in the flashing flow.

Example 3 shows a case in which the production rate is reduced for the unit and the light ends absorber control pressure is also reduced. This case shows that by lowering the control pressure, the ratio of flashing flow to MeOH feed flow is reduced to a lower value than Example 1 indicating improved operation. Example 4 shows a case similar to Example 3 with the control pressure lowered even further. Again, the result is a reduction in the flash flow (second mass flow rate) to MeOH feed flow (first mass flow rate) ratio as shown in Table 3. The pressure is reported in atm (gauge) for the vapor discharge in the absorber system, top of the light ends column, and flash vessel. Mass flows are reported as the relative mass flow to the methanol feed mass flow in Example 1.

TABLE 3

| Pressure (atm) | Example 1 | Example 2 | Example 3 | Example 4 |
|---|---|---|---|---|
| Absorber System | 1.85 | 1.84 | 0.58 | 0.48 |
| Light Ends Column | 1.99 | 1.94 | 0.70 | 0.61 |
| Flash Vessel | 2.18 | 2.16 | 0.87 | 0.79 |
| A. MeOH Feed Mass Flow | 100 | 83.65 | 65.21 | 65.21 |
| B. Reaction Medium Mass Flow | 937.96 | 984.26 | 554.28 | 544.31 |
| Mass Flow Ratio (B/A) | 9.38 | 11.77 | 8.50 | 8.35 |

If the system included separate pressure controllers for the light ends column and/or the flash vessel, the flash vessel pressure would necessarily be higher in all examples which would result in a higher flash flow to MeOH feed flow causing additional operating and raw material expenses. A higher pressure is needed to operate the separate pressure controls devices.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

I claim:

1. A process for producing acetic acid comprising:
    introducing methanol to a reactor at a first mass flow rate;
    carbonylating the methanol in the reactor in the presence of a metal catalyst, iodide salt, water, and methyl iodide to form a reaction medium comprising acetic acid;
    separating the reaction medium in a flash vessel into a liquid recycle stream and a vapor product stream comprising acetic acid, wherein the reaction medium is withdrawn at a second mass flow rate; and
    adjusting the internal pressure of the flash vessel to maintain a mass flow ratio of the second mass flow rate to the first mass flow rate of less than or equal to 10.

2. The process of claim 1, wherein the internal pressure of the flash vessel is adjusted to maintain the mass flow ratio of the second mass flow rate to the first mass flow rate from 1 to 10.

3. The process of claim 1, wherein the pressure of the flash vessel is adjusted in response to backpressure from a downstream vapor discharge.

4. The process of claim 1, wherein the internal pressure in the flash vessel is adjusted within a range from 0.5 to 5 atm gauge.

5. The process of claim 1, further comprising withdrawing a gaseous purge stream from the reactor to an absorption system, wherein the absorption system comprises a high pressure absorption tower and a low pressure absorption tower.

6. The process of claim 2, wherein the gaseous purge stream comprises carbon monoxide, hydrogen, methane, carbon dioxide, acetic acid, methyl acetate, methyl iodide, hydrogen iodide, acetaldehyde, dimethyl ether, and water.

7. The process of claim 2, wherein at least a portion of the gaseous purge stream is fed to the high pressure absorption tower.

8. The process of claim 7, wherein the high pressure tower operated at a pressure of greater than or equal to 0.7 atm gauge.

9. The process of claim 1, wherein the mass flow ratio of the second mass flow rate to the first mass flow rate is from 1 to 10.

10. The process of claim 1, wherein the total reactor internal pressure of the reactor is from 15 to 40 atm absolute.

11. The process of claim 1, wherein the water in the reactor is maintain to be from 0.1 to 14 wt. %.

12. The process of claim 1, further comprising:
    distilling a portion of the vapor product stream in a light ends column into an overhead and a side stream comprising acetic acid;
    partially condensing the overhead into a liquid stream and gaseous stream; and
    withdrawing a portion of the gaseous stream to an absorption system, wherein the absorption system comprises a high pressure absorption tower and a low pressure absorption tower.

13. The process of claim 12, wherein the portion of the gaseous stream is fed to the low pressure absorption tower.

14. The process of claim 13, further comprising regulating a vapor discharge from the low pressure absorption tower to control the pressure in the flash vessel and the light ends column.

* * * * *

UNITED STATES PATENT AND TRADEMARK OFFICE
CERTIFICATE OF CORRECTION

PATENT NO. : 11,685,706 B2
APPLICATION NO. : 17/021576
DATED : June 27, 2023
INVENTOR(S) : Ronald D. Shaver Page 1 of 1

It is certified that error appears in the above-identified patent and that said Letters Patent is hereby corrected as shown below:

On the Title Page

Item (71) Applicant: Please delete "Celanese International Corporation Inc." and insert -- Celanese International Corporation --

Signed and Sealed this
Thirtieth Day of January, 2024

Katherine Kelly Vidal
*Director of the United States Patent and Trademark Office*